United States Patent
Bublewitz et al.

(10) Patent No.: US 7,498,363 B2
(45) Date of Patent: Mar. 3, 2009

(54) TWO-COMPONENT DENTAL MOLDING MATERIAL MADE OF HYDROXYL-FUNCTIONAL POLYETHERS AND ALKOXYSILANES OR SILICIC ACID ESTERS

(75) Inventors: Alexander Bublewitz, Herborn (DE); Jens-Peter Reber, Meinerzhagen (DE)

(73) Assignee: Kettenbach GmbH & CO. KG, Eschenburg (DE)

( * ) Notice: Subject to any disclaimer, the term of this patent is extended or adjusted under 35 U.S.C. 154(b) by 591 days.

(21) Appl. No.: 11/230,067

(22) Filed: Sep. 19, 2005

(65) Prior Publication Data

US 2006/0069179 A1 Mar. 30, 2006

(30) Foreign Application Priority Data

Sep. 17, 2004 (DE) ........................ 10 2004 045 214

(51) Int. Cl.
*A61K 6/10* (2006.01)
*C08L 83/04* (2006.01)
*A61C 9/00* (2006.01)

(52) U.S. Cl. .................... 523/109; 524/588; 528/44; 433/214

(58) Field of Classification Search ................ 523/109; 524/588; 528/44
See application file for complete search history.

(56) References Cited

U.S. PATENT DOCUMENTS

| | | | |
|---|---|---|---|
| 4,798,878 A | 1/1989 | Brinkmann et al. | |
| 4,906,707 A | 3/1990 | Yukimoto et al. | |
| 5,118,290 A * | 6/1992 | Muller et al. | ................. 433/48 |
| 6,218,461 B1 | 4/2001 | Schwabe et al. | |
| 6,503,994 B1 | 1/2003 | Nehren et al. | |
| 6,790,903 B1 * | 9/2004 | Majolo et al. | ................ 524/506 |
| 6,835,760 B2 | 12/2004 | Schaub et al. | |
| 7,091,298 B2 | 8/2006 | Schindler et al. | |
| 2002/0147275 A1 | 10/2002 | Bublewitz et al. | |
| 2002/0156186 A1 * | 10/2002 | Bublewitz et al. | ........... 525/100 |

FOREIGN PATENT DOCUMENTS

| | | |
|---|---|---|
| DE | 197 53 456 | 6/1999 |
| DE | 198 08 557 | 9/1999 |
| DE | 199 42 467 | 4/2001 |
| DE | 100 61 195 | 6/2002 |
| DE | 101 03 446 | 8/2002 |
| DE | 101 04 079 | 8/2002 |
| DE | 101 39 132 | 2/2003 |
| EP | 0 170 865 | 2/1986 |
| EP | 0 372 561 | 6/1990 |
| EP | A 0 492 412 | 7/1992 |
| EP | A 0 492 413 | 7/1992 |
| EP | A 0 541 972 | 5/1993 |
| EP | 0 723 807 | 2/1997 |
| EP | 0 269 819 | 6/1998 |
| EP | 0 956 980 A1 | 11/1999 |
| EP | 1 303 560 | 1/2002 |
| EP | 1 226 808 | 7/2002 |
| EP | 1 339 373 | 9/2003 |
| WO | PCT/EP98/01993 | 4/1998 |
| WO | PCT/EP00/05418 | 6/2000 |
| WO | PCT/EP02/05916 | 7/2001 |
| WO | PCT/EP01/13852 | 11/2001 |
| WO | WO 02/58 641 | 1/2002 |
| WO | WO 02/08323 | 1/2002 |

OTHER PUBLICATIONS

"Isocyanatomethyl-dimethylmonomethoxysilane—A Building Block for RTV-2 Systems", 2nd European Organosilicon Days, Programs & Abstracts, by W. Ziche.

Ullman's Encyclopädie der Technischen Chemie (Encyclopedia of technical chemistry), vol. 21, p. 523.

Schriftenreihe Pigmente Degussa Kieselsäuren/Degussa pigment monograph series, silicic acids, No. 12, p. 5, as well as No. 13, p. 3. 2000.

"Isocyanatomethyl-dimethylmonomethoxysilane—A Building Block for RTV-2 Systems", 2nd European Organosilicon Days, Programs & Abstracts, by W. Ziche 2003.

Ullman's Encyclopädie der Technischen Chemie (Encyclopedia of technical chemistry), vol. 21, p. 523, undated.

ZM 93, No. 15, p. 32 ff, undated.

* cited by examiner

*Primary Examiner*—Tae H Yoon
(74) *Attorney, Agent, or Firm*—Collard & Roe, P.C.

(57) ABSTRACT

Condensation-crosslinking two-component dental molding materials based on polyethers are particularly suitable for taking impressions. Such materials are used in dental medicine, for example for taking tooth impressions, for bite registration, or for lining dental prostheses. The molding material is made of the following:

a) at least one hydroxylsilyl-functional polyether;
b) at least one alkoxysilane $b_1$) or one polysilicic acid ester $b_2$);
c) at least one reinforcing filler $c_1$) having a BET surface of at least 50 $m^2/g$ or at least one non-reinforcing filler $c_2$) having a BET surface of less than 50 $m^2/g$,
d) water, if necessary; and
e) at least one condensation catalyst.

12 Claims, No Drawings

TWO-COMPONENT DENTAL MOLDING MATERIAL MADE OF HYDROXYL-FUNCTIONAL POLYETHERS AND ALKOXYSILANES OR SILICIC ACID ESTERS

BACKGROUND OF THE INVENTION

1. Field of the Invention

The present invention relates to condensation-crosslinking two-component dental molding materials based on polyethers, which are particularly suitable for taking impressions, as well as mixtures that can be obtained from them, and their use. Such materials are used in dental medicine, for example for taking tooth impressions, for bite registration, or for lining dental prostheses.

2. The Prior Art

Condensation-crosslinking dental molding materials usually contain hydroxyl-functional polymers with a silicon backbone, which crosslink and cure in the presence of water and metallorganic compounds, for example organic tin or titanium compounds. However, such materials are comparatively hydrophobic, because of the silicon backbone of the polymers, so that significant proportions of surfactant must be added to them, for the purpose of reducing the surface tension and to adjust the required wettability.

As an alternative to this, two-component dental molding materials are known that contain polymers having terminal alkoxysilyl groups and a hydrophilic polyether backbone, which demonstrate sufficiently hydrophilic properties for wetting of the moist tooth substance. Usually, these materials consist of a base component containing alkoxysilyl-functional polyether having an average molecular weight of 800 to 20,000 g/mol, which can also have urea and/or urethane groups, as a function of their synthesis, fillers, as well as any other necessary additives, and a catalyst component that contains not only fillers and any other necessary additives but also an organic and/or inorganic acid as the catalyst.

Condensation-crosslinking two-component dental molding materials are known from EP 0 269 819 B1, the base component of which contains polyaddition products containing alkoxysilyl end groups, having a predominantly linear molecular structure and an average molecular weight of 800 to 20,000 g/mol, which have a content of polyether groups of 25 to 90 wt.-%, a content of urethane groups of 0.5 to 10 wt.-%, a content of urea groups of 0.5 to 10 wt.-%, as well as a content of terminal alkoxysilyl groups of 1 to 25 wt.-%, and the catalyst component of which contains a mixture containing water as well as organic and/or inorganic acids in weight amount ratios (water/acid) of 1:0.01 to 1:40.

European Patent No. EP 1 226 808 A2 discloses condensation-crosslinking two-component dental molding materials consisting of a base component and a catalyst component, the base component of which contains alkoxysilyl-functional polyethers having a linear or branched main chain and an average molecular weight of 800 to 20,000 g/mol, which have a content of polyether groups of 20 to 95 wt.-%, a content of terminal alkoxysilyl groups of 0.2 to 25 wt.-%, as well as a content of urethane groups or urea groups of up to 10 wt.-%, if necessary, and the catalyst component of which contains a mixture containing water as well as organic and/or inorganic acids in weight amount ratios of 1:0.01 to 1:40. Preferably, the catalyst component contains p-toluene sulfonic acid hydrate as the catalyst, and a polyether diol and additional additives, such as fillers, paraffin, emulsifier, and the like.

However, the known dental materials based on alkoxysilyl ethers have the disadvantage of binding with insufficient rapidity. Furthermore, the catalyst mixture, which according to the state of the art must necessarily contain an acid, is limited with regard to the chemical nature and the amount of fillers that can be added, so that special additives, such as emulsifiers and/or thickeners, must be added to it, so that the two components can be mixed using mixer systems that are usual on the market. Because of the lack of flexibility with regard to the addition of fillers, the components of the dental material must furthermore be specially formulated in order to obtain components to be mixed in a ratio of 1:1.

SUMMARY OF THE INVENTION

It is therefore an object of the present invention to make available a hydrophilic condensation-crosslinking two-component dental molding material based on polyethers, which demonstrates faster binding kinetics as compared with those previously known, is flexible with regard to the chemical nature and amount of fillers to be added to the catalyst component, and furthermore can easily be formulated in the form of 1:1 systems.

According to the invention, this task is accomplished by means of a condensation-crosslinking two-component dental molding material containing a) at least one hydroxylsilyl-functional polyether, b) at least one alkoxysilane $b_1$) and/or one polysilicic acid ester $b_2$), c) at least one reinforcing filler $c_1$) having a BET surface of at least 50 m²/g and/or at least one non-reinforcing filler $c_2$) having a BET surface of less than 50 m²/g, d) water, if necessary, as well as e) at least one condensation catalyst.

Surprisingly, it was found, within the scope of the present invention, that condensation-crosslinking two-component dental molding materials that contain at least one hydroxylsilyl-functional polyether a) as well as at least one alkoxysilane $b_1$) and/or one polysilicic acid ester $b_2$) in place of the alkoxysilyl-functional polyether that is conventionally used, bind more quickly than materials that contain alkoxysilyl-functional polyethers.

Furthermore, it was found that the two-component dental materials according to the invention, containing, in combination, at least one hydroxylsilyl-functional polyether as well as at least one alkoxysilane and/or one polysilicic acid ester can be crosslinked and cured not only by means of acids, as described in the state of the art for dental materials that exclusively contain alkoxysilyl-functional polyethers, but also with other condensation catalysts, such as bases and metallorganic compounds, with reaction kinetics that are suitable for dental materials. Therefore the systems according to the invention are also more flexible than the materials previously known, with regard to the chemical nature and the amount of the fillers to be added to the catalyst component.

Fundamentally, all the polyethers containing hydroxylsilyl groups that are known to a person skilled in the art can be used as hydroxylsilyl-functional polyethers a), whereby the polyether backbone can be linear and/or branched, and can be composed, for example, of polyethylene oxide, polypropylene oxide, polytetrahydrofuran and/or their copolymers, whereby these monomers can be present statistically, in blocks, or in a tactical arrangement. Monovalent or multivalent alcohols can be used as starters for the polyethers and/or copolymers, such as, for example, methanol, butanol, glycerin, trimethyl propane, pentaerythrite, and sorbitol. For example, copolymers of polytetrahydrofuran with polyethylene oxide or of polyethylene oxide and polypropylene oxide can be used, whereby pure polypropylene oxide is particularly preferred. Furthermore, polyethers having side-position alkyl groups are preferred, whereby every or at least every tenth monomer structural unit carried a side-position alkyl group.

Preferably, the hydroxylsilyl-functional polyethers a) have a numerically average molecular weight from 200 to 250,000 g/mol, particularly preferably from 400 to 100,000 g/mol, and very particularly preferably from 1,000 to 20,000 g/mol.

According to a special embodiment of the present invention, the hydroxylsilyl structural unit(s) of the at least one polyether a) is/are disposed exclusively terminally, with reference to the polymer backbone, and fall under the general formula $SiR^1R^2R^3$, where $R^1$, $R^2$, $R^3$, independent of one another, are hydrogen, alkyl, or hydroxy, with the proviso that at least one radical is a hydroxyl group. Particularly preferably, the at least one polyether has a hydroxyl group content of 0.08 to 7.0 mmol/g, particularly preferably of 0.1 to 5, and very preferably of 0.1 to 1.0 mmol/g.

Preferably, the at least one hydroxylsilyl-functional polyether a) has a content of polyether groups between 1 and 30 mmol/g and particularly preferably between 2 and 25 mmol/g.

In another embodiment of the invention polyethers a) are used that have alkylene spacers disposed on the preferably terminal hydroxylsilyl groups, in each instance, as the third structural unit, which spacers particularly preferably have $C_1$-$C_6$ alkyl groups, and very particularly preferably $C_1$-$C_3$ alkyl groups, and most highly particularly preferably methylene groups.

Furthermore, the at least one polyether a) can have 0 to 8 mmol/g, particularly preferably 0 to 4 mmol/g, and very particularly preferably 0.02 to 2 mmol/g urethane groups, and/or 0 to 8 mmol/g and particularly preferably 0 to 2 mmol/g urea groups as the fourth structural unit, as a function of the synthesis.

For example, the individual structural units of the at least one polyether a) can be disposed according to one of the following general formulas (I) and (II):

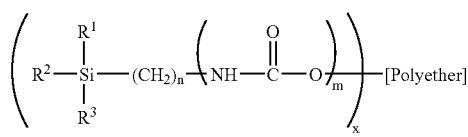

Formula (I)

where x=1 to 6, preferably x=2 to 4, and very particularly preferably x=2, n=1 to 6, preferably n=1 to 3, and very particularly preferably n=1, as well as m=0 or 1, particularly preferably m=1, and $R^1$, $R^2$, $R^3$, independent of one another, are hydrogen, alkyl, or hydroxyl, with the proviso that at least one radical is a hydroxyl group, preferably $R^1$ and $R^3$, independent of one another, are alkyl, as well as $R^2$=hydroxyl and particularly preferably, $R^1$ and $R^3$=methyl as well as $R^2$=hydroxyl, and/or

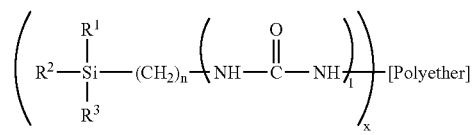

Formula (II)

where x=1 to 6, preferably x=2 to 4, and very particularly preferably x=2, n=1 to 6, preferably n=1 to 3, and very particularly preferably n=1, as well as l=0 or 1, particularly preferably l=1, and $R^1$, $R^2$, $R^3$, independent of one another, are hydrogen, alkyl, or hydroxyl, with the proviso that at least one radical is a hydroxyl group, preferably $R^1$ and $R^3$, independent of one another, are alkyl, as well as $R^2$=hydroxyl and particularly preferably, $R^1$ and $R^3$=methyl as well as $R^2$=hydroxyl.

The production of these hydroxylsilyl-functional polyethers is known and is described, for example, in W. Ziche, "Isocyanatomethyl-dimethylmonomethoxysilane—A Building Block for RTV-2 Systems," $2^{nd}$ European Organosilicon Days, Programs & Abstracts, which is herein incorporated by reference.

Particularly good results are obtained, however, if the at least one hydroxylsilyl-functional polyether a) is a linear polyether, whereby linear polyethers having the general formula (III):

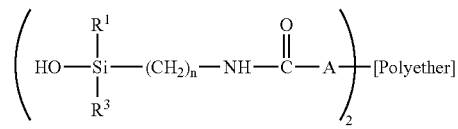

wherein A=NH or O, $R^1$, $R^2$ independent of one another, are alkyl, aryl, aralkyl, preferably methyl, n is a whole number between 1 and 6, preferably between 1 and 3, and particularly preferably 3

[Polyether]=[$CH_2$—O]$_{n1}$, [$CH_2$—$CH_2$—O]$_{n2}$, [$CH_2$—C($CH_3$)H—O]$_{n3}$, [C($CH_3$)H—$CH_2$—O]$_{n4}$, [$CH_2$—$CH_2$—$CH_2$—$CH_2$—O]$_{n5}$ oder or [$CH_2$—CRH—O]$_{n6}$, where R is alkyl, aryl, aralkyl, $n_1$ is a whole number between 1 and 500, preferably between 1 and 10, $n_2$ is a whole number between 1 and 1,000, preferably between 1 and 20, $n_3$, $n_4$ independent of one another, are a whole number between 1 and 1,500, preferably between 1 and 300, $n_5$ is a whole number between 1 and 100, preferably between 1 and 15, and $n_6$ is a whole number between 1 and 1500, preferably between 1 and 300, are very particularly preferred.

According to a special embodiment of the present invention, the condensation-crosslinking two-component dental molding material contains at least one hydroxylsilyl-functional polyether a) according to the general formula (IV)

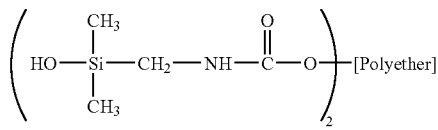

and/or the general formula (V)

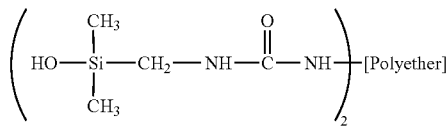

Preferably, the two-component dental material according to the invention contains 10 to 80 wt.-%, particularly preferably 20 to 70 wt.-%, and very particularly preferably 30 to 70 wt.-% of at least one polyether a) that contains hydroxylsilyl groups, with reference to the total mixture.

Fundamentally, any alkoxysilanes $b_1$) that are known to persons skilled in the art can be used within the scope of the present invention, whereby, however, good results can be achieved in particular with compounds having the general formula (VI):

$$Si(OR^5)_x R^6_y$$

where x is a whole number between 1 and 4, preferably $x \leq 3$, y=4−x, preferably $y \leq 1$, $R^5$, independent of one another, are alkyl, aryl, acyl, preferably methyl or ethyl, $R^6$, independent of one another, are alkyl, alkenyl, aryl, acyl, (meth)acryloxy alkyl, amino(cyclo)alkyl, amino acryl, preferably methyl, ethyl, or vinyl.

Particularly preferred examples for silanes $b_1$) to be used according to the invention are tetraalkoxysilanes, particularly tetramethoxysilane and tetraethoxysilane, as well as trialkoxysilanes, particularly vinyl trimethoxysilane and vinyl triethoxysilane.

According to the invention, the two-component dental material contains at least one polysilicic acid ester $b_2$), in place of or in addition to the alkoxysilane $b_1$), which is preferably a compound having the general formula (VII):

$$(R^5O)_{x1} R^7_{y2} - Si - [O - Si(OR^5)_2]_n - OSiR^7_{y2}(OR^5)_{x2}$$

where $x_1$, $x_2$, independent of one another, are whole numbers between 0 and 3, preferably $x_1 = x_2 \geq 1$, $y_1 = 3 - x_1$, $y_{2=3} - x_2$, preferably $y_1 = y_2 \leq 2$, n is a whole number between 0 and 50, preferably between 0 and 25, particularly preferably between 0 and 10, and very particularly preferably 1, $R^5$, independent of one another, are alkyl, aryl, acyl, preferably methyl or ethyl, $R^7$, independent of one another, are alkyl, alkenyl, aryl, acyl, preferably methyl, ethyl, or vinyl.

Within the scope of the present invention, it has been shown that particularly good results are achieved if the dental molding material contains 0.1 to 5.0%, particularly preferably 0.2 to 4.0%, and very particularly preferably 0.2 to 3.0% of at least one alkoxysilane $b_1$) and/or 0.1 to 3.0%, particularly preferably 0.1 to 2%, and very particularly preferably 0.1 to 1.0% of at least one polysilicic acid ester $b_2$).

According to a first embodiment of the present invention, the at least one catalyst e) is an acid, whereby organic or inorganic acids are preferred. In particular, sulfuric acid, phosphoric acid, dibutyl phosphoric acid, trifluoromethane sulfonic acid, tartaric acid, citric acid, adipinic acid, benzoic acid, 2-ethyl caproic acid or alkanic acid, and particularly preferably, p-toluene sulfonic acid have proven themselves to be particularly suitable, alone or in mixtures with one another.

In this embodiment, the catalyst component B, with reference to the total mixture, contains 0.01 to 2 wt.-%, particularly preferably 0.05 to 1.0 wt.-%, and very particularly preferably 0.05 to 0.5 wt.-% of at least one acid e).

According to a second embodiment of the present invention, the two-component dental molding materials according to the invention contain at least one base and/or one salt from a base with an acid as the catalyst e), whereby with the exception of inorganic bases, such as alkali metal hydroxides, alkali metal carbonates, and the like, which are unsuitable for dental medicine applications because of their toxicological hazardousness and/or because of overly slow reaction kinetics, fundamentally all known bases, particularly organic bases, Lewis bases, basic ion exchanger resins, strong, sterically hindered bases and superbases are suitable for this purpose.

Particularly preferably, the two-component dental materials contain at least one strong, sterically hindered base as the catalyst e). Within the scope of the present invention, it was surprisingly found that when using strong, sterically hindered bases, in comparison with the use of other bases, only a very slight catalyst concentration is necessary in order to obtain dental material having suitable reaction kinetics, particularly a sufficiently long working and curing time. Because of the low amount of catalyst required, the resulting dental materials also demonstrate outstanding biocompatibility. Furthermore, in this manner, reaction kinetics with a snap effect, as described in EP 1 226 808 A2, which is hereby introduced as a reference and thereby considered to be part of the disclosure, are achieved. Furthermore, this catalyst system demonstrates good storage stability, and is neutral in terms of odor and taste, in contrast to dental impression materials on the basis of aziridinopolyethers, as they are disclosed, for example, in International Application No. PCT/EP02/05916, German Patent No. DE 197 53 456, and International Application No. PCT/EP01/13852.

Fundamentally, the two-component dental materials according to the invention can contain any of the strong, sterically hindered bases known to a person skilled in the art as the catalyst e), whereby $(CH_3)_2NC(=NH)N(CH_3)_2$ 1,1,3,3-tetramethylguanidine

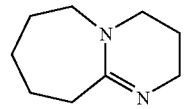

1,8-diazabicyclo[5.4.0]undec-7-ene (DBU),

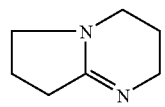

1,5-diazabicyclo[4.3.0]non-5-ene (DBN)

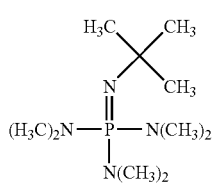

tert-butylimino-tris(dimethylamino)phosphoran

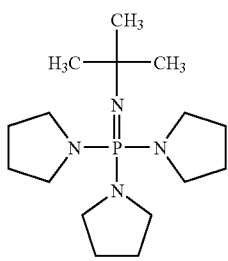

tert-butylimino-tri(pyrrolidino)phosphoran

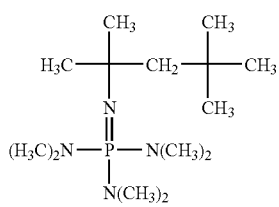

tert-octylimino-tris(dimethylamino)phosphoran

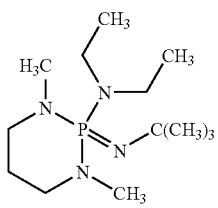

2-tert-butylimino-2-diethylamino-1,3-dimethyl-perhydro-1,3,2-diazaphosphorine

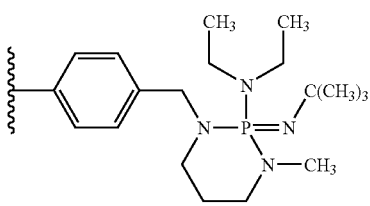

2-tert-butylimino-2-diethylamino-1,3-dimethyl-perhydro-1,3,2-diazaphosphorine on polystyrene

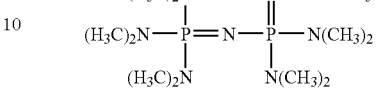

1-tert-butyl-2,2,4,4,4-pentakis(diethylamino)-2Λ5,4Λ5-catenadi(phosphazene)

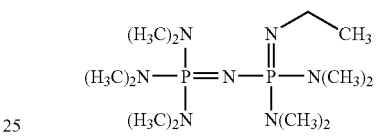

1-ethyl-2,2,4,4,4-pentakis(diethylamino)-2Λ5,4Λ5-catenadi(phosphazene)

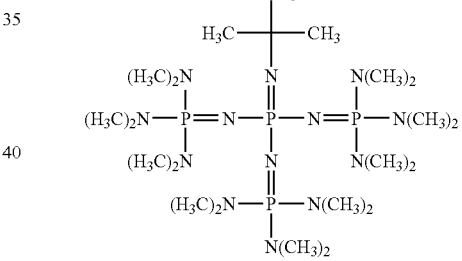

1-tert-butyl-4,4,4-tris(dimethylamino)-2,2-bis[tris(dimethylamino)-phosphoranylidenamino]-2Λ$^5$, 4Λ$^5$-catenadi (phosphazene)

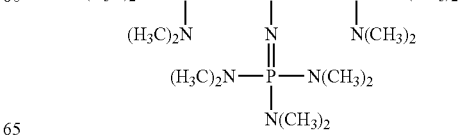

1-tert-octyl-4,4,4-tris(dimethylamino)-2,2-bis[tris(dimethylamino)-phosphoranylidenamino]-2Λ$^5$, 4Λ$^5$-catenadi(phosphazene)

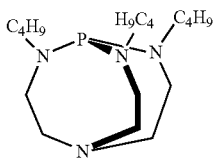

2,8,9-triisobutyl-2,5,8,9-tetraaza-1-phosphabicyclo[3.3.3]undecane

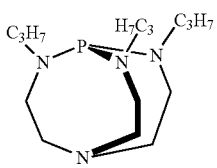

2,8,9-triisopropyl-2,5,8,9-tetraaza-1-phosphabicyclo[3.3.3]undecane

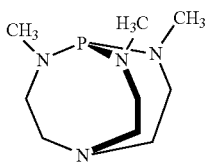

2,8,9-trimethyl-2,5,8,9-tetraaza-1-phosphabicyclo[3.3.3]undecane as well as 2-tert-butyl-1,1,3,3-tetramethylguanidine, N,N-dicyclohexylmethylamine, N,N-diethylaniline, N,N-diisopropyl-2-ethylbutylamine, N,N-diisopropylmethylamine, N,N-diisopropyl-3-pentylamine, N,N-dimethylaniline, 2,6-di-tert-butyl-4-methylpyridine, 1,5,7-triazabicyclo(4.4.0)dec-5-ene, 7-methyl-1,5,7-triazabicyclo(4.4.0)dec-5-ene, 1,5-diazabicyclo(4.3.0)non-5-ene, 1,1,3,3-tetramethylguanidine, quinuclidine, 2,2,6,6-tetramethylpiperidine, pempidine, tributylamine, triethylamine, N-ethyldiisopropylamine, 3,3,6,9,9-pentamethyl-2,10-diazabicyclo-(4.4.0)dec-1-ene, N,N,N'N'-tetramethyl-1,8-naphthalenediamine, 2,4,6-tri-tert-butylpyridine, and tris(trimethylsilyl)amine are particularly preferred as strong, sterically hindered bases. 1,1,3,3-tetramethylguanidine, DBU, and DBN are particularly preferred as the base catalyst.

All of the bases e) mentioned above can be used individually or in any desired combination with one another, in each instance. Preferably toxically compatible bases are used, which are sufficiently basic to demonstrate a sufficient catalytic effect even when used in small concentrations, and, if necessary, to achieve an additional effect, for example in connection with the desensitization of teeth.

A further development of the invention uses at least one salt from a base with an acid in place of or in addition to the at least one base as the catalyst e). Preferably, the at least one salt is either a salt from a strong, sterically hindered base with a weak acid, or a salt from a weak base with a strong acid.

Particularly preferred examples of salts to be used according to the invention, produced from a strong base with a weak acid, are salts of diazabicycloundecane and/or 1,5-diazabicyclo[4.3.0]non-5-ene with alkanic acids, fatty acids, ethyl caproic acid, ascorbinic acid, salicylic acid, acetylsalicyclic acid, or benzoic acid. The acids last mentioned are preferably used for salt formation also because they demonstrate not only high catalysis activity but also medicinal substance properties, as well as a preservative and/or antioxidant effect. Particularly preferred examples of salts to be used according to the invention, from strong acids with a weak base are salts of toluene sulfonic acid with pyridine or toluene sulfonic acid with N,N-2-,4-,6-pentamethylaniline. Aside from toluene sulfonic acid, sulfuric acid, fluorosulfonic acid, trifluoromethane sulfonic acid, or fluorosulfuric acid can also be used as strong acids, for example, whereas pyridine, pentamethylaniline, and pyrrol are other preferred examples of weak bases.

The use of at least one salt from a base with an acid is advantageous for several reasons. For one thing, a salt, in contrast to the use of a free base, or, as provided in the state of the art, a free acid, brings about a moderate pH. For the salt pair of a sterically hindered base with a weak acid, for example DBU with ethyl caproic acid, the pH preferably lies between 8 and 11, and particularly preferably between 8 and 9, whereas for the salt pair of a strong acid with a weak base, for example toluene sulfonic acid with pyridine, the pH is preferably between 2 and 7, and particularly preferably between 3 and 4. Because of these moderate pH values, good compatibility of the dental materials according to the invention with the mucous membranes of the mouth and with the tooth enamel is guaranteed, so that no etching or irritation will occur. Furthermore the moderate pH values of the stated catalyst salts, in other words the salts from a base with an acid, preferably of a strong base with a weak acid or of a strong acid with a weak base, impart an excellent storage stability to the dental materials, since these salts, in contrast to free acids or bases, are chemically inert with regard to the other ingredients of the dental material, and thus do not enter into any secondary reactions or decomposition reactions with other ingredients, such as with fillers, for example, with the polyether used as a paste formation agent, or with the alkoxysilyl polyether, particularly during the storage period and after curing. In contrast to the stated catalyst salts e), strong bases, for example, attach the cristobalite that is frequently used as a filler in dental materials, or strong acids attack polyether and alkoxysilyl polyether, whereby the free base or the free acid, respectively, is used up and therefore the catalyst activity that was originally adjusted is reduced. This results in a longer curing time, or in an extreme case, actually prevents curing. A polymer decomposition as the result of secondary or decomposition reactions after curing would furthermore result in a lack of shape stability; such shape stability, however, is an absolute prerequisite for making a mold and producing a model.

Another advantage of the use of the catalyst salts e) provided according to the invention lies in the avoidance of interactions between the catalyst and active substance additives, since the pH can be directly adjusted to the requirements of the active substance by means of selecting a suitable catalyst salt, and therefore an unrestricted effectiveness of the active substances is guaranteed. Furthermore, the dental materials according to this embodiment demonstrate good biocompatibility, because of the surprisingly low concentrations of the stated catalyst salts that are required. Finally, the dental materials according to this embodiment are also characterized by excellent neutrality in terms of odor and taste, which is an important property for a dental molding material, in order to achieve patient acceptance and avoid gagging reactions of the patient during application.

Preferably, the dental materials according to the invention contain 0.001 to 1 mmol/g, particularly preferably 0.001 to 0.5, and very particularly preferably 0.001 to 0.1 mmol/g of at least one base, which is preferably a strong, sterically hindered base, and/or 0.001 to 1.0 mmol/g, particularly preferably 0.001 to 0.5, and very particularly preferably 0.001 to 0.1 mmol/g of at least one salt from a strong base with a weak acid, and/or 0.0005 to 0.5 mmol/g, particularly preferably 0.0005 to 0.25, and very particularly preferably 0.0005 to 0.05 mmol/g of at least one salt from a weak base with a strong acid, in the catalyst component B, with reference to the total mixture.

In the case of the first and second embodiment, in other words when using at least one acid, one base, or one salt from an acid and a base as the catalyst e), the at least one alkoxysilane $b_1$) and/or the at least one silicic acid ester $b_2$) are preferably contained in the component A, and the at least one hydroxylsilyl-functional polyether a), the water d), if it is provided, and the catalyst e) are contained in the component B.

The water d) that is possibly contained in the catalyst component B leads to the formation of silanol groups, by means of reaction with the alkoxy groups of the silane $b_1$) or the silicic acid ester $b_2$), which groups in turn represent the reactive species for the condensation reaction. Preferably, the catalyst component B of the two-component dental molding material according to the invention contains 0.001 to 3%, particularly preferably 0.005 to 2%, and very particularly preferably 0.01 to 1.5% water d), with reference to the total mixture.

It has proven to be advantageous that the molar ratio of water to alkoxy groups, with reference to the total mixture, amounts to between 1:6 and 1:1.5, and particularly preferably between 1:4 and 1:2. Within the scope of the present invention, it has surprisingly been shown that reaction kinetics in keeping with dental requirements, in other words a comparatively long working time at a comparatively short dwell time in the mouth, with snap effect, is achieved if the water content of the total mixture is lower than the alkoxy group content of the total mixture.

According to a third embodiment of the present invention, the at least one catalyst e) is a metallorganic compound, preferably a metal alkoxide, a chelate and/or an oligocondensate or polycondensate of a metal alkoxide, a double metal alkoxide, in other words an alkoxide that contains two different metals in a specific ratio, a metal acylate, and/or a metal carboxylate. Examples of suitable metal alkoxides are those selected from among the group consisting of aluminum alkoxide, antimony alkoxide, barium alkoxide, boron alkoxide, calcium alkoxide, cerium alkoxide, erbium alkoxide, gallium alkoxide, silicon alkoxide, germanium alkoxide, hafnium alkoxide, indium alkoxide, iron alkoxide, lanthanium alkoxide, magnesium alkoxide, neodynium alkoxide, samarium alkoxide, strontium alkoxide, tantalum alkoxide, titanium alkoxide, tin alkoxide, vanadium alkoxide, yttrium alkoxide, zinc alkoxide, zirconium alkoxide, and mixtures of them.

Particularly preferably, the at least one metallorganic compound is a titanium organic, zirconium organic, and tin organic compound, whereby titanium tetraethylate, titanium tetrapropylate, titanium tetraisopropylate, titanium tetrabutylate, titanium tetraisooctylate, titanium isopropylate tristeaorylate, titanium triisopropylate steaorylate, titanium diisopropylate disteaorylate, titanium triisopropylate-O-allyloxy (polyethylenylate), titanium allylacetoacetate triisopropylate, titanium bis(triethanolamine) diisopropylate, titanium chloride triisopropylate, titanium di-n-butylate (bis-2,4-pentane dionate), titanium dichloride diethylate, titanium diisopropylate bis-(2,4-pentane dionate), titanium diisopropylate bis(tetramethylheptane dionate), titanium tetraisobutylate, titanium dilactate, titanium methacrylate triisopropylate, zirconium tetrapropylate, zirconium tetraisopropylate, zirconium tetrabutylate, zirconium tetraethylate, zirconium hexafluoropentane dionate, zirconium dimethacrylate, zirconium trifluoropentane dionate, zirconium dimethacrylate dibutylate, tin dibutyl laurate, tin dibutyl mercaptide, tin dibutyl dicarboxylate, tin dioctyl dicarboxylate, tin bis(2-ethoxyhexaonate), tin bis(neodecanoate), tin tetraallylate, tin tetramethylate, tin tetravinylate, tin dimethyl hydroxyoleate, dialkyl tin diacetate, tin (II) octoate, dialkyl tin diacylate, dialkyl tin oxide are very particularly preferred.

In the case of this third embodiment, the hydroxylsilyl-functional polyether a) as well as the water d), if it is provided, are preferably contained in the component A, and the alkoxysilane $b_1$) and/or the silicic acid ester $b_2$) as well as the catalyst e) are contained in the component B.

Preferably, the catalyst component B contains 0.1 to 3.0%, particularly preferably 0.1 to 2.0%, and very particularly preferably 0.1 to 1.5% of at least one metallorganic compound as the catalyst e), with reference to the total mixture.

According to the invention, the component A of the dental molding material according to the invention contains at least one reinforcing filler $c_1$) and/or at least one non-reinforcing filler $c_2$), whereas the catalyst component B does not have to contain any filler. Preferably, however, the component B also contains at least one reinforcing filler $c_1$) and/or at least one non-reinforcing filler $c_2$).

Highly disperse, active fillers having a BET surface of at least 50 $m^2$/g are particularly suitable as reinforcing fillers $c_1$). Those having an individual particle size in the nanometer range, which can be present as aggregates and/or agglomerates, are particularly suitable. Preferably, the at least one reinforcing filler $c_1$) is selected from the group that consists of aluminum hydroxide, zinc oxide, titanium oxide, zirconium oxide, silicon dioxide, as well as precipitated and/or pyrogenic silicic acid. Of course, the compounds mentioned above can be used individually or in any desired combination with one another, specifically also both in hydrophilic and in hydrophobized form.

Furthermore preferably, the at least one reinforcing filler $c_1$) is present in the form of nanoparticles, as a fiber-form or lamella-form filler, for example a mineral fiber-form filler, or as a synthetic fiber-form filler.

In a further development of the invention, the reinforcing filler $c_1$) provided in the component that contains the alkoxysilane $b_1$) and/or the silicic acid ester $b_2$) has a water content of maximally 0.5 wt.-%, particularly preferably of maximally 0.3 wt.-%, and very particularly preferably of maximally 0.15 wt.-%, whereby the water content is determined by way of Karl Fischer titration, according to the invention.

According to a special embodiment of the present invention, the at least one reinforcing filler $c_1$) in the base component A has a pH between 5 and 9, and particularly preferably between 5.5 and 8.5. In this manner, degradation of the hydroxylsilyl-functional polyethers during storage is avoided.

Preferably, the base component A of the dental molding material according to the invention contains 0 to 50 wt.-%, particularly preferably 0.1 to 40 wt.-%, and very particularly preferably 0.1 to 30 wt.-%, with reference to the component A, and the catalyst component B contains 0 to 50 wt.-%, particularly preferably 0.1 to 40 wt.-%, and very particularly preferably 0.1 to 30 wt.-% of at least one reinforcing filler $c_1$), with reference to the component B.

Fundamentally, the same substances as for the reinforcing fillers are suitable as non-reinforcing fillers $c_2$), whereby the non-reinforcing fillers necessarily have a BET surface of less than 50 m²/g (Schriftenreihe Pigmente Degussa Kieselsäuren/Degussa pigment monograph series, silicic acids/, No. 12, page 5, as well as No. 13, page 3). Preferably the at least one non-reinforcing filler is a substance selected from among the group that consists of earth alkali metal oxides, earth alkali metal hydroxides, earth alkali metal fluoride, earth alkali metal carbonates, calcium apatite ($Ca_5[(F, Cl, OH, \frac{1}{2}CO_3|(PO_4)_3]$, particularly calcium hydroxyl apatite ($Ca_5[(OH)|(PO_4)_3]$, titanium dioxide, zirconium dioxide, aluminum hydroxide, silicon dioxide, precipitated silicic acid, and calcium carbonate. Of course, the compounds mentioned above can be used individually or in any desired combination with one another, specifically also both in hydrophilic and in hydrophobized form.

Preferably, the non-reinforcing fillers $c_2$) that are used have an average grain size greater than 0.1 μm (Ullmann's Encyclopädie der Technischen Chemie [Encyclopedia of technical chemistry], Volume 21, page 523).

In a further development of the invention, the non-reinforcing filler $c_2$) provided in the component that contains the alkoxysilane $b_1$) and/or the silicic acid ester $b_2$) has a water content of maximally 0.5 wt.-%, particularly preferably maximally 0.1 wt.-%, and very particularly preferably maximally 0.05 wt.-%.

According to a special embodiment of the present invention, the at least one non-reinforcing filler $c_2$) in the base component A has a pH between 5 and 9, and particularly preferably between 5.5 and 8.5, in order to prevent degradation of the hydroxyl-functional polyethers during storage.

Preferably, the base component A of the dental molding material according to the invention contains 0 to 80 wt.-%, particularly preferably 0.05 to 75 wt.-%, and very particularly preferably 0.1 to 70 wt.-%, with reference to the component A, and the catalyst component B contains 0 to 80 wt.-%, particularly preferably 0.05 to 75 wt.-%, and very particularly preferably 0.1 to 70 wt.-% of at least one non-reinforcing filler $c_2$), with reference to the component B.

In total, the total content of fillers $c_1$), $c_2$) is preferably 0.01 to 80 wt.-%, particularly preferably 0.05 to 75 wt.-%, and very particularly preferably 0.1 to 70 wt.-%, with reference to the total mixture.

In a further development of the invention, exclusively acid-stable ingredients are added to the dental materials according to the first embodiment of the present invention, in which at least one acid is used as the catalyst e), and exclusively base-stable ingredients are added to the dental materials according to the second embodiment of the present invention, in which at least one base and/or at least one salt from strong bases and weak acids is used as the catalyst e), and to add exclusively acid-stable ingredients to the dental materials according to the second embodiment of the present invention, in which at least one salt from weak bases and strong acids is used as the catalyst e). Base-stable and acid-stable in the sense of the present invention refers to compounds that are so base-stable or acid-stable, even after a storage period of at least 12 months, that no noticeable deterioration of the reaction kinetics that were originally adjusted occurs.

According to another special embodiment of the present invention, the reinforcing and non-reinforcing fillers $c_1$), $c_2$) contained in the catalyst component B have a pH between 3.5 and 12. If free, strong, sterically hindered bases are used as the catalyst e), the catalyst component B preferably contains base-stable fillers $c_1$), $c_2$) having a pH between 6.0 and 12.0, and very particularly preferably those having a pH between 7.0 and 11.0. In the case of salts from strong, sterically hindered bases with weak acids as the catalyst, base-stable fillers having a pH between 6.0 and 11.0 are preferably used in the catalyst component B, and very particularly those having a pH between 7.0 and 10.0 are used. If salts from strong acids with weak bases are used as the catalyst e), the catalyst component B preferably contains base-stable fillers having a pH between 3.5 and 9.0, and very particularly preferably those having a pH between 5.0 and 8.5.

In a further development of the invention, one or more of the following additives and/or ancillary substances are added to the dental molding material according to the invention:

f) buffer salts,
g) water catchers,
h) paste forming agents,
I) surfactant,
j) active substance,
k) plasticizer,
l) substance allowing optical scanning,
m) flavor and/or fragrance,
n) substance allowing diagnosis,
o) fluoridation agent,
p) bleach substance,
q) desensitization agent,
r) adhesion bond imparting agent,
s) dye,
t) indicator,
u) stabilizer (antioxidant),
v) antibacterial substance.

Buffer salts f) can optionally be added to the dental molding material according to the invention, with which the pH of the catalyst component B and of the base component A can be adjusted. Buffer systems having a buffer salt selected from among the group consisting of alkali metal hydrogen carbonate, dialkali hydrogen phosphate, tris(hydroxymethyl)aminomethane, phthalic acid monoalkali salt, phthalic acid monotetramethyl ammonium salt, ammonium salts of amines, cyclic amines, amides, cyclic amides, and 4,4'-(oxidi-2,1-ethane-diyl)bismorpholine have proven themselves to be particularly suitable for this purpose. As a person skilled in the art will recognize, the addition of a buffer system f) is particularly practical for the first and second embodiment of the present invention, in which a free acid or a free base is used as the catalyst. Such an addition can, however, of course also be advantageous in the embodiment of the present invention in which a salt from a base with an acid is used as the catalyst, or in the third embodiment of the present invention, in which a metallorganic compound is used as the catalyst e).

According to another special embodiment of the present invention, the dental materials, specifically in the component that contains the alkoxysilane $b_1$) and/or the silicic acid $b_2$), have at least one water catcher g), which is preferably selected from among the group that consists of alkoxysilanes, titanates, such as tetraisopropyltitanate, zirconates, such as tetrapropylzirconate, zeoliths, aluminum sulfate, anhydrous calcium sulfate (for example Drierite®), blue gel, and oxazolidines.

In a further embodiment of the invention, one or more functional alkoxysilanes are used as water catchers g), since the crosslinking speed, the structure, and the properties of the resulting elastomer can be adjusted by means of such compounds. Preferably, the at least one functional alkoxysilane is a compound having the general formula (VIII)

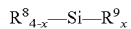

where $R^8$=H, alkyl, alkenyl, —$(CH_2)$—X, where n=1 to 6, $R^9$=alkoxy,
X=$NH_2$, $NHR^{10}$, $NR_2$, whereby $R^{10}$=alkyl, aminoalkyl, —CO, —$OCH_3$, as well as X=0, 1, 2, 3, or 4,
whereby particularly preferably, $R^8$=alkenyl or —$(CH_2)_n$—X with X=$NHR^{10}$ and n=1 or 3, and/or x=3 or 4 and $R^{10}$=—$OCH_3$.

Particularly preferably, the at least one functional alkoxysilane g) is vinyl trimethoxysilane and/or N-trimethoxysilylmethyl-O-methylcarbamate. The two compounds just mentioned are reactive silanes that not only increase the crosslinking speed during curing, but also function as water catchers g) for removing any traces of water that are still present in the component A of the dental composition, and thereby prevent a premature viscosity increase or crosslinking of the alkoxysilyl polyether during storage. Furthermore, by means of adding vinyl trimethoxysilane, which is installed into the elastomer network during the condensation reaction, the mechanical property of the cured dental material can be adjusted. In particular in the case of the dental molding materials according to the invention which have hydroxylsilyl polyether a) with a methylene spacer at the terminal alkoxysilyl groups, it has proven to be advantageous to add both vinyl trimethoxysilane and N-trimethoxysilylmethyl-O-methylcarbamate to the component A, since here, the reactivity of vinyl trimethoxysilane alone is frequently not sufficient for stabilization with regard to water. Furthermore, N-trimethoxysilylmethyl-O-methylcarbamate in the component A leads to high cross-linking of the products resulting from the condensation reaction, after mixing with the catalyst component, and therefore results in cured dental materials having high tear strength, good elasticity, and good recovery properties.

Alternatively or in addition to vinyl trimethoxysilane and/or N-trimethoxysilylmethyl-O-methylcarbamate, 3-(2-aminoethylamino)propyltrimethoxysilane can preferably also be added to the dental molding materials according to the invention, as a functional silane. This compound represents a highly basic catalyst, on the one hand, and a crosslinking agent, on the other hand. Because of the basic properties of the amino group, this substance reacts in a strongly alkaline manner, so that in the presence of water, silanols are formed with hydrolysis and release of methanol, which silanols crosslink by way of Si—O—Si bonds.

Furthermore, the two-component dental molding materials according to the invention preferably contain, particularly preferably in the catalyst component B, at least one paste forming an agent h), since the latter allows the adjustment of a paste-like consistency, for example having low viscosity, medium viscosity, or high viscosity, as well as homogeneous mixing of the aqueous base and the solid reinforcing and non-reinforcing fillers $c_1$), $c_2$) Preferably, a compound selected from among the group that consists of polyethers, polyvinyl pyrrolidones, polyurethanes, polyesters, waxes, Vaseline, paraffin oils, silicon oils, glycerin, propylene glycols, polypropylene glycols, ethylene glycols, polyethylene glycols, copolymerizates of N-vinyl pyrrolidine and vinyl acetate, carboxymethylcellulose, methylcellulose, hydroxyethylcellulose, hydroxypropylcellulose, polysaccharides, glycerin, and poly(meth)acrylic acids, is used as at least one paste forming agent h). Of course, the dental molding materials according to the invention can also contain any desired combination of two or more of the aforementioned compounds. When using a free acid or a free, strong, sterically hindered base in the catalyst component B, those of the aforementioned compounds that are acid-stable or base-stable, respectively, are very particularly preferred, so that these do not react with the acid or base contained in the catalyst component B during storage, using up hydronium or hydroxide ions, so that even after an extended storage period, the base concentration of the catalyst component B and therefore the working and curing time of the dental molding materials according to the invention remains constant.

The compounds I) that might be used as a surfactant, emulsifier, and/or stabilizer are preferably anionic surfactants, particularly preferably alkyl sulfates, alkylbenzol sulfonates, or alkylbenzol phosphates, cationic surfactants, particularly preferably tetraalkylammonium halogenides, non-ionic surfactants, particularly preferably alkyl and alkylphenyl polyalkylalkylene oxides, fatty acid alkoxylates, fatty alcohol alkyloxylates, as well as their alkyl ethers and alkyl esters, fatty acid alkylolamides, saccharose fatty acid esters, trialkylaminoxides, silicon surfactants, or fluorine surfactants, or amphoteric surfactants, particularly preferably sulfated or oxyethylated condensation products of alkenyl phenols and formaldehyde, ethylene oxide-propylene oxide block polymerizates, or modified polysiloxanes. In addition or as an alternative to this, derivatives of the aforementioned surfactants can also be used, for example those that have functional groups such as —OH, —CH=$CH_2$, —OCO—$(CH_3)$C=$CH_2$, as well as alkoxysilyl groups. Furthermore, other surfactants known to a person skilled in the art can be used, although these are less preferred.

Furthermore, the dental molding materials according to the invention can contain one or more active substances j) that are contained in the base component A or the catalyst component B, depending on their chemical functionality. The active substances to be used according to the invention include, in particular, astringents such as epinephrine, substances having an antibacterial and/or antifungal effect, such as hexitidine (for example 5-amino-1,3-bis(2-ethylhexyl)-5-methylhexahydropyrimidine), triclosanes (for example 2,4,4'-trichloro-2-hydroxydiphenylether) and chlorhexidine:

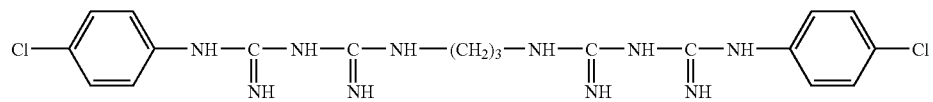

Possible plasticizers k) are, in particular, non-reactive polyethers, polyesters, polyurethanes, phthalates, monoesters, diesters, triesters, or esters having a higher valence, particularly acetyltributyl citrate, phthalates, and alkylsulfonic acid esters of phenol, which are added to the component A and/or the component B, depending on their chemical nature.

Compounds l) that allow optical readability/scanning can be any substances known to a person skilled in the art for this purpose, particularly metal powders, metal pigments, metallic pigments, and titanium dioxide, which are added to the component A and/or the component B, depending on their chemical nature.

Furthermore, the dental materials according to the invention can contain usual flavors and/or, fragrances m) and/or additives n) that are useful for diagnosis in one of the two or in both components, as they are described, for example, in European Patent No. EP 1 339 373, International Application No. PCT/EP00/05418, and German Patent No. DE 100 61 195.

Sodium fluoride, potassium fluoride, ammonium fluoride, fluorophosphates, and aminofluorides, such as N'-octadecyl-bimethylenediamine-N,N,N'-bis(2-ethanol)-dihydrofluoride (as described in ZM 93, No. 15, page 32 ff.) have proven to be suitable as fluoridation aids o), which can also be added to the component A and/or the component B), depending on their chemical nature.

Furthermore, the dental molding material according to the invention can contain one or more different peroxides in the component A and/or the component B, as a bleach substance p), which are preferably selected from the group that consists of alkali metal and earth alkali metal peroxides, hydrogen peroxide, as well as carbamide peroxide.

Examples of suitable desensitization agents q) are potassium salts, such as potassium nitrate, clove oil, and eugenol.

Alkoxysilanes, epoxysilanes, aminosilanes, and methacrylate silanes are particularly suitable as adhesion bond imparting agents r), for example for forming an adhesion bond between the molding material and a molding tray made of stainless steel and/or plastic.

Examples of suitable dyes s) are dye pigments in the form of Al, Ca, Ba oxides/lacquered dye, which can be added to the component A and/or the component B, depending on their chemical nature, like the ancillary substances described above, unless otherwise indicated.

Furthermore, dye indicators t) can be added to the dental molding materials according to the invention, in the component A and/or the component B, which change their color as a function of the pH, for example because of changes in pH that occur when the components A and B are mixed, or upon contact with water.

Compounds selected from the group that consists of polymer trimethyl-dihydroquinoline, diphenyl derivatives, phenothiazine, phenyl-α-naphthylamine, 4,4'-methylene-bis-2, 6-di-tert.-butylphenol, butylhydroxyanisol (BHA), and methoxyphenol (hydroxyanisol), in particular, can be added to the two-component dental materials according to the invention as stabilizers and/or antioxidants u). Examples of such compounds are the products commercially available from the Ciba-Geigy company, Irganox® 1010 1076, 1035, MD 1024, Irgafos® 168, 38, Irgacor® 252 LD/252FC, 1405, 1930, 153, Tinuvin® 328, P, 384, 900, 928, 327, 1130, 400, 292, 144, 123, 622, as well as Chimassorb® 119.

Preferably, the two-component dental material according to the invention is stored in suitable primary packaging, such as tubes and jars, and particularly preferably in cartridges and tubular bags, as they are described, for example, in European Patent No. EP 0 723 807 A2, European Patent No. EP-A-0 541 972, International Application No. PCT/EP/980193, European Patent No. EP-A-0 492 412, European Patent No. EP-A-0 492 413, and European Patent No. EP 0 956 980 A1, which are herein incorporated by reference, and proportioned in customized amounts for later use.

Another object of the present invention is mixtures that can be obtained by means of mixing the components A and B of the two-component dental molding material according to the invention as described above. Preferably, the base component A is mixed with the catalyst component B in a ratio of 1:2 to 20:1, particularly preferably from 1:1 to 10:1, and very particularly preferably 10:1, 5:1, 4:1, 2:1, and 1:1. These mixtures are characterized by excellent wettability and an outstanding flow behavior on moist tooth and tissue substance. Despite these good hydrophilic properties, the material does not swell upon contact with aqueous media, such as water, saliva, blood, disinfection bath, or aqueous plaster paste. The good initial wettability of the mixture is important for detailed, accurate molding of the molding material in the patient's mouth during working and during the first contact with moist mouth/tooth substance, and is expressed by a low contact angle of less than 60°, preferably less than 50°, and particularly preferably less than 40°, measured using a contact angle measuring device from the Krüss company, at 20° C., with the "lying drop" measuring method. Furthermore, the cured molding material at the time plaster is cast into it (immediately or 2 hours after curing) is also characterized by a contact angle of less than 60°, preferably less than 50°, and particularly preferably less than 40°.

Accordingly, while only a few embodiments of the present invention have been shown and described, it is obvious that many changes and modifications may be made thereunto without departing from the spirit and scope of the invention.

What is claimed is:

1. A two-component dental molding material comprising:
   a) at least one hydroxylsilyl-functional polyether a);
   b) at least one alkoxysilane $b_1$) of formula VI

   $Si(OR^5)_x R^6_y,$ where x is a whole number between 1 and 4,
   y=4−x,
   $R^5$, independent of one another, are alkyl, aryl, or acyl, and
   $R^6$, independent of one another, are alkyl, alkenyl, aryl, acyl, (meth)acryloxy alkyl, amino(cyclo)alkyl, or amino acryl,
   or at least one polysilicic acid ester $b_2$) of formula VII

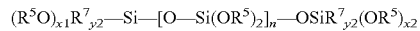
   $(R^5O)_{x1}R^7_{y2}-Si-[O-Si(OR^5)_2]_n-OSiR^7_{y2}(OR^5)_{x2}$ where $x_1$, $x_2$, independent of one another, are whole numbers between 0 and 3,
   $y_1=3-x_1$, $y_2=3-x_2$,
   n is a whole number between 0 and 50,
   $R^5$, independent of one another, are alkyl, aryl, or acyl, and
   $R^7$, independent of one another, are alkyl, alkenyl, aryl, or acyl,
   or a combination of at least one alkoxysilane $b_1$) of formula VI and of at least one polysilicic acid ester $b_2$) of formula VII;
   C) at least one reinforcing filler $c_1$) having a BET surface of at least 50 m²/g or at least one non-reinforcing filler $c_2$) having a BET surface of less than 50 m²/g, or a combination of said at least one reinforcing filler $c_1$) and of said at least one non-reinforcing filler $c_2$);
   d) 0 to 3% by weight, referring to the total composition, of water d); and
   e) at least one condensation catalyst e), said two-component dental molding material comprising a first component A and a second component B, wherein component A comprises the alkoxysilane $b_1$) or the polysilicic acid ester $b_2$) or a combination of the alkoxysilane $b_1$) and of the polysilicic acid ester $b_2$), and the reinforcing filler $c_1$) or the non-reinforcing filler $c_2$, and component B comprises the hydroxysilyl-functional polyether a), optionally the water d), the condensation catalyst e) and optionally the reinforcing filler $c_1$) or optionally the non-reinforcing filler $c_2$) or optionally a combination of the reinforcing filler $c_1$) and the non-reinforcing filler $c_2$), or wherein component A comprises the hydroxysilyl-functional polyether a), the reinforcing filler $c_1$) or the non-reinforcing filler $c_2$) or a combination of the reinforcing filler $c_1$) and the non-reinforcing filler $c_2$), and optionally the water d), and component B comprises the alkoxysilane $b_1$) or the polysilicic acid ester $b_2$) or a combination of the alkoxysilane $b_1$) and of the polysilicic acid ester $b_2$), the condensation catalyst, and optionally the reinforcing filler $c_1$) or optionally the reinforcing filler $c_2$) or optionally a combination of the reinforcing filler $c_1$) and the non-reinforcing filler $c_2$).

2. A dental molding material according to claim 1, wherein the at least one hydroxylsilyl-functional polyether a) has hydroxylsilyl structural units that are disposed exclusively terminally in the polymer backbone, and fall under the general formula $SiR^1R^2R^3$, where $R^1$, $R^2$ and $R^3$, independent of one another, are hydrogen, alkyl, or hydroxy, and at least one of $R^1$, $R^2$ and $R^3$ is a hydroxyl group.

3. A dental molding material according to claim 1, wherein the at least one hydroxylsilyl-functional polyether a) has a hydroxyl group content of 0.08 to 7.0 mmol/g.

4. A dental molding material according to claim 1, wherein individual structural units of the at least one hydroxylsilyl-functional polyether a) have one of the following general formulas (I) and (II):

Formula (I)

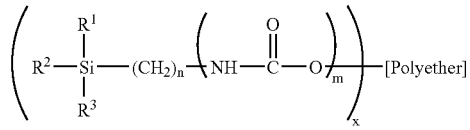

where x=1 to 6
n=1 to 6,
m=0 or 1, and
$R^1$, $R^2$, $R^3$, independent of one another, are hydrogen, alkyl, or hydroxyl, and at least one of $R^1$, $R^2$ and $R^3$ is a hydroxyl group, and Formula (II)

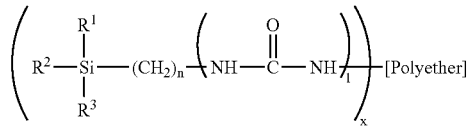

where x=1 to 6,
n=1 to 6,
l=0 or 1, and
$R^1$, $R^2$, $R^3$, independent of one another, are hydrogen, alkyl, or hydroxyl, and at least one of $R^1$, $R^2$ and $R^3$ is a hydroxyl group.

5. A dental molding material according to claim 1, wherein the hydroxylsilyl-functional polyether a) has the general formula (IV)

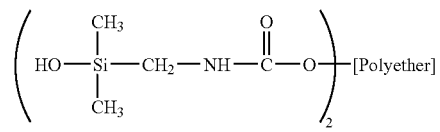

or the general formula (V)

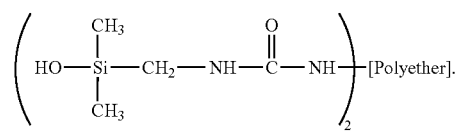

6. A dental molding material according to claim 1, wherein the material contains 10 to 80 wt.-% of the at least one polyether a) that contains hydroxylsilyl groups.

7. A dental molding material according to claim 1, wherein the material contains 0.1 to 5.0% of said at least one alkoxysilane $b_1$) or 0.1 to 3.0% of said at least one polysilicic acid ester $b_2$).

8. A dental molding material according to claim 1, wherein the at least one condensation catalyst e) is an organic or inorganic acid or an organic base.

9. A dental molding material according to claim 1, wherein the the alkoxysilane $b_1$) or the silicic acid ester $b_2$) are contained in the first component A, and the hydroxylsilyl-functional polyether a), the water d) and catalyst e) are contained in the second component B.

10. A dental molding material according to claim 1, wherein the at least one condensation catalyst e) is a metallorganic compound.

11. A dental molding material according to claim 10, wherein the hydroxylsilyl-functional polyether a) as well as the water d), are contained in the first component A, and the alkoxysilane $b_1$) and/or the silicic acid ester $b_2$) as well as the catalyst e) are contained in the second component B.

12. A mixture that can be obtained by mixing components A and B of the two-component dental molding material according to claim 11, wherein the component A is mixed with the catalyst component B in a ratio of 1:2 to 20:1.

* * * * *